US006368637B1

(12) United States Patent
Stoneburner

(10) Patent No.: US 6,368,637 B1
(45) Date of Patent: Apr. 9, 2002

(54) METHOD AND COMPOSITION FOR TOPICAL TREATMENT OF VIRAL LESIONS

(75) Inventor: Jon Stoneburner, Sarasota, FL (US)

(73) Assignee: Cross Bay LLC, Las Vegas, NV (US)

( * ) Notice: Subject to any disclaimer, the term of this patent is extended or adjusted under 35 U.S.C. 154(b) by 0 days.

(21) Appl. No.: 09/828,119

(22) Filed: Apr. 9, 2001

(51) Int. Cl.$^7$ .................. A61K 31/498; A61K 33/20; A61K 41/00; A61M 35/00
(52) U.S. Cl. .............. 424/665; 424/661; 424/662; 424/663; 424/664; 514/250; 514/934; 422/28; 422/29; 422/37; 604/20; 604/289; 604/290
(58) Field of Search ................. 424/661–665; 514/250, 934; 422/28, 29, 37; 604/20, 289, 290; 607/88

(56) References Cited

PUBLICATIONS

Medline abstract, accession No. 75165887 (1975).*
Embase abstract, accession No. 78346405 (1978).*
Medline abstract, accession No. 76216141 (1976).*

* cited by examiner

*Primary Examiner*—John Pak
(74) *Attorney, Agent, or Firm*—Dennison, Scheiner & Schultz

(57) ABSTRACT

A process for treating active viral lesions, such as herpes lesions and warts, on persons or animals, in which an active lesion containing a virus is scrubbed or debrided, an aqueous reagent solution containing neutral red and free chlorine is applied to the scrubbed lesion, and the lesion to which the reagent has been applied is exposed to ultraviolet light for a period sufficient to cause viral destruction. The invention further relates to the aqueous reagent solution containing neutral red and free chlorine.

13 Claims, No Drawings

METHOD AND COMPOSITION FOR TOPICAL TREATMENT OF VIRAL LESIONS

BACKGROUND OF THE INVENTION

1. Field of the Invention

The invention relates to the field of topical treatments for topical viral infections, especially herpes simplex infections and warts.

2. Description of Related Art

The herpes simplex virus (HSV) is a common cause of infections of the skin and mucous membranes, and may also cause more serious infections in other parts of the body. There are two distinct types of the virus, HSV-1 which usually infects the oral cavity and which is not sexually transmitted, and HSV-2, which is known as genital herpes and which is sexually transmitted. Both types of the virus, may however, be found at any area of the body.

HSV infections have become extremely widespread; it is estimated that about 20% of Americans will have a positive blood test for HSV-2.

Other types of the herpes virus are responsible for other infection, with herpes zoster being responsible for chicken pox and human herpesvirus 8 thought to be responsible for Kaposi's sarcoma.

When HSV enters the human body, it penetrates vulnerable cells in the lower layers of the skin, and attempts to replicate itself in the cell nuclei, thereby destroying the cells and causing the blisters and inflammation characteristic of the infection. The resulting skin lesions are often tiny blisters grouped together on an inflamed base. Viral particles are carried from the skin through branches of nerve cells to clusters at nerve cell ends called ganglia. The HSV in the ganglia enters an inactive or latent state in which replication does not occur but in which the virus survives. While infection is not evident during the latent period, but the virus may begin to multiply again, causing symptoms. With HSV-1, there is recurrence of infection in 20 to 40% of cases, while with HSV-2, there is a much higher rate of recurrence, up to 80%. Recurrences usually occur at the same site, and while the cause of this renewed infection is not completely known, factors such as sunlight, wind, fever, local injury, menstruation, suppression of the immune system and emotional stress are thought to be involved.

HSV infections trigger the body's immune system, and in healthy people, infections tend to become less severe and less frequent. However, the immune system cannot completely eradicate the virus.

HSV is transmitted by skin-to-skin contact, often by sexual contact and kissing. While those with active sores are much more infectious than those without symptoms, a person does not need to have a visible lesion or ulcer to be infectious. One cannot predict when a person is shedding the virus.

While there is no cure for herpes infections, oral acyclovir has been found to be an effective treatment for patients with first or recurrent episodes of herpes, interfering with the ability of the virus to reproduce itself. While treatment of a primary infection with acyclovir will shorten the duration of lesions and decrease infectiousness, the virus remains in the body for life. Moreover, a small number of patients experience side effects from acyclovir, including headache, nausea, vomiting, rash and impaired kidney function.

A number of topical treatments are known for active lesions, including topical antiviral medicines. Other topical treatments include those disclosed in U.S. Pat. Nos. 4,657,933 and 4,657,934, directed to ethyl ether-based compositions.

Warts are another type of topical viral infection. Warts are caused by viruses in the human papillomavirus (HPV) family. The main types of warts are common warts, found on the elbows, arms and face, molluscum contagiosum, found on the face, back and shoulders, plantar warts, found on the soles of the feet and genital warts, found in the genital area and anus.

Warts may be treated with salicylic acid preparations commonly sold over the counter, or with more sophisticated therapies such as cryotherapy, electrodessication, curretage and laser therapy.

SUMMARY OF THE INVENTION

It is therefore an object of the invention to provide a safe and effective treatment for herpes lesions, warts and other topical viral infections with minimal side effects.

To achieve this and other objects, the invention is directed to a method for treatment of topical viral lesions by scrubbing the lesions, and applying thereto an aqueous reagent solution comprising neutral red and free chlorine. The site is then irradiated with ultraviolet light, 40–400 nm wavelength for a period of time effective to destroy the infected cell without causing burns to the skin.

DETAILED DESCRIPTION OF THE INVENTION

The treatment process of the invention falls into a category known as "phototherapy" in which a lesion is treated with a particular compound, then exposed to light of a defined wavelength to treat the lesion. Porphyrins are known for use in phototherapy, as disclosed, for example, in U.S. Pat. Nos. 4,753,958, 4,925,736 and 5,399,583. U.S. Pat. No. 4,235,887 discloses chemically combining a drug with another moity by a photocleavable bond, and irradiating a diseased area with UV radiation to cleave the bond and release the drug.

Neutral red, known chemically as $N^8N^{8,}$3-trimethyl, 2,8-phenazinediamine monohydrochloride, is a green powder soluble in water to yield a red color. The compound is known as a pH indicator and as a biological stain.

The treatment composition of the invention is a water solution of neutral red and free chlorine, the chlorine typically being supplied by sodium hypochlorite. A neutral red concentration as low as about 0.01% by weight is thought to be effective, although about 0.05 to 0.1% is preferred. Higher concentrations, e.g. up to 1% by weight may be used but are not though to provide any additional advantage.

Chlorine in very small amounts, about 1 ppm by weight, is thought to be effective, and thus, chlorine in the amount found in tap water will provide some effectiveness in a treatment composition according to the invention. Amounts of 10 to 500 ppm are preferred, and while higher concentrations, e.g. up to 10,000 ppm (1%) may be used, they are not thought to provide any additional advantage.

The composition is typically prepared in a dispensing vial containing 5 mg neutral red. To the vial is added 10 ml of bacteriostatic water suitable for injection, USP (containing 0.9% benzyl alcohol, which is not in itself an element of the invention) to which has been added 1 drop of 6 weight% sodium hypochlorite. The composition thus prepared contains by weight, approximately 0.05% neutral red and 0.02% sodium hypochlorite, the solution containing about 0.005% free chlorine.

In practice, the solution is prepared just before use by adding the water to the neutral red vial with a sterile hypodermic needle.

The patient to be treated should have active lesions, and should be tested to confirm the presence of HSV-1 or HSV-2virus. The affected area should be scrubbed and, if necessary, debrided. If vesicles or sacs are left unopened and not fully exposed, the effectiveness of the treatment is diminished., The specific treatment procedure will depend on the type of outbreak. If the lesion is on the face or other exposed area, the area is simply scrubbed to remove any scabs, and the vesicles or sacs are broken or punctured, which may be accomplished with a jewelers forceps or small tweezers. Topical anesthetic may be applied as necessary. If the lesion in on the gum line, a mild acid wash is used to debride the affected area.

Exposed lesions on the genitalia or anus are scrubbed or debrided to the extent possible. For lesions within the vagina or rectum, an acidic douche or enema is used to debride the affected tissue. Preparation of an area affected by genital warts also requires that the lesion area be debrided, and while the entire lesion does not need to be removed, the surface of each lesion must be opened.

For treatment of exposed sites, the vial in which the composition is contained should have an applicator top. Standard medicine vials have a rubber stopper at one end which can be penetrated by a needle for withdrawal of medication; for purposes of the invention, a vial could be used with a rubber stopper at one end and a wick or applicator at the other end.

The vial which is used for application should be used once only and discarded; it should not be used on another patient.

For areas which are not easily exposed, the solution may be applied by flushing the area with a plastic hypodermic syringe.

After the solution is applied, the area is exposed to ultraviolet light for a period of time necessary for effective treatment, but not so long as to result in a burn of the area. Ultraviolet light is defined as having a wavelength in the range of about 295 to 400 nm, although the lamps which are commonly used are in the middle UV range, about 280–320 nm. UV lamps having a power of 15 to 25 watts are commonly used, and these should be held close to the lesion, a distance of about 1–3 inches being preferable.

Application of UV will cause a sensation of "tingling" in the lesion area; when the "tingling" vanishes, the treatment is terminated. While the actual time of treatment will vary depending on the wavelength of the UV source, the intensity of the source and the distance from the lesion, the average time of treatment is at least about 10 minutes. Treatment times greater than 20 minutes are to be avoided as the affected area may burn.

When the lesion is not in an exposed area, such as the mouth, the vagina or the rectum, a UV light source which is narrow, e.g. less than one-half inch in diameter may be used; such sources are commonly used in dentistry to set polymers in the mouth. When used in the vagina or rectum, the light source should be coated with a lubricant such as KY® jelly or creme.

The treated area should be subsequently cleaned with soap and water. The area will have a red or pink colored stain which will persist for several days.

While not wishing to be held to any particular theory, it is thought that the reagent applied to the lesion is absorbed by the cell wall of the virus, and interacts with the protein of the cell wall. When the cell is exposed to UV light, a reaction occurs which causes the cell wall to expand to approximately 300–400 times its original size. This reaction thus causes the virus to "explode" into numerous fragments which become targets for the formation of antibodies.

Normally, the virus multiplies faster than the body can make antibodies, but when the virus is reduced to fragments, the body recognizes the foreign proteins, and antibodies are rapidly produced.

What is claimed is:

1. A process for treating active topical viral lesions on persons or animals in need of treatment, comprising the steps of:
   scrubbing or debriding an active lesion containing a virus;
   applying to the scrubbed lesion an aqueous reagent solution comprising neutral red and free chlorine; and
   exposing the lesion to which the reagent solution has been applied to ultraviolet light for a period of time sufficient to cause viral destruction.

2. The process of claim 1, wherein the exposing is continued for a period of time necessary for a tingling sensation in the lesion to cease.

3. The process of claim 1, wherein the lesion is exposed for a period of at least ten minutes.

4. The process of claim 1, wherein the exposing step is terminated before burning of the lesion take place.

5. The process of claim 1, wherein the debriding is chemical debriding with an aqueous acid solution.

6. The process of claim 1, wherein the reagent solution contains at least about 0.01% by weight neutral red and at least about 0.0001% by weight free chlorine.

7. The process of claim 6, wherein the reagent solution contains about 0.05% by weight neutral red and about 0.005% by weight free chlorine.

8. The process of claim 1, additionally comprising the step of washing the lesion after said exposing with soap and water.

9. The process of claim 1, wherein the debriding comprises puncturing vesicles or sacs in the lesions.

10. The process of claim 1, wherein the lesions are herpes simplex lesions.

11. The process of claim 1, wherein the lesions are warts.

12. The process of claim 1, wherein the lesion to which the reagent has been applied is exposed to an ultraviolet lamp producing radiation in the range of 280–320 nm, and having a power of 15–25 watts.

13. A composition for treatment of herpes lesions by phototherapy, comprising, by weight, an aqueous solution containing, by weight, at least about 0.01% neutral red and at least about 0.001% free chlorine.

* * * * *